US008801712B2

(12) United States Patent
Felix et al.

(10) Patent No.: US 8,801,712 B2
(45) Date of Patent: Aug. 12, 2014

(54) RADIOLUCENT BONE PLATE WITH RADIOPAQUE MARKER

(75) Inventors: Brent A Felix, Sandy, UT (US); David N McKean, Bountiful, UT (US); David A Hershgold, Draper, UT (US)

(73) Assignee: Innovasis, Inc., Salt Lake City, UT (US)

( * ) Notice: Subject to any disclaimer, the term of this patent is extended or adjusted under 35 U.S.C. 154(b) by 11 days.

(21) Appl. No.: 12/719,765

(22) Filed: Mar. 8, 2010

(65) Prior Publication Data

US 2011/0218570 A1  Sep. 8, 2011

(51) Int. Cl.
*A61B 17/56* (2006.01)
*A61B 17/58* (2006.01)
*A61B 17/80* (2006.01)
*A61F 2/30* (2006.01)

(52) U.S. Cl.
USPC ............................. 606/71; 606/70; 606/280

(58) Field of Classification Search
USPC ........ 606/280–299, 70, 71; 623/23.72–23.76, 623/23.51–23.61
See application file for complete search history.

(56) References Cited

U.S. PATENT DOCUMENTS

| | | | |
|---|---|---|---|
| 1,828,287 A | 10/1931 | Macbean | |
| 2,405,909 A | 8/1946 | Smith | |
| 3,455,360 A | 7/1969 | Simons | |
| 4,329,743 A * | 5/1982 | Alexander et al. | 623/13.18 |
| 4,403,606 A | 9/1983 | Woo et al. | |
| 4,512,038 A | 4/1985 | Alexander et al. | |
| 4,623,290 A | 11/1986 | Kikuzawa et al. | |
| 4,778,637 A | 10/1988 | Adams et al. | |
| 4,863,330 A | 9/1989 | Olez et al. | |
| 4,863,470 A | 9/1989 | Carter | |
| 5,127,783 A | 7/1992 | Moghe et al. | |
| 5,209,888 A | 5/1993 | Shimada et al. | |
| 5,246,655 A | 9/1993 | Mitchell et al. | |
| 5,466,237 A | 11/1995 | Byrd, III et al. | |
| 5,474,555 A | 12/1995 | Puno et al. | |
| 5,540,870 A | 7/1996 | Quigley | |
| 5,676,146 A | 10/1997 | Scarborough | |
| 5,807,051 A | 9/1998 | Heminger | |
| 5,951,556 A | 9/1999 | Faccioli et al. | |

(Continued)

FOREIGN PATENT DOCUMENTS

DE      44 43 051 A1    10/1996
DE     100 65 799 C1    4/2002

(Continued)

OTHER PUBLICATIONS

PCT/US2011/024935, May 23, 2011, International Search Report and Written Opinion.

(Continued)

*Primary Examiner* — Matthew Lawson
*Assistant Examiner* — Si Ming Lee
(74) *Attorney, Agent, or Firm* — Workman Nydegger (57) ABSTRACT

A bone plate has a main body configured to position adjacent bones with respect to each other. The main body includes a plurality of separate layers bonded together. Each layer is comprised of a radiolucent material and has a first aperture and a second aperture that extend through the layer. The layers are all stacked such that the first apertures of all of the layers are aligned with each other and the second apertures of all of the layers are aligned with each other. An insert can be positioned within the first aperture.

15 Claims, 11 Drawing Sheets

(56) References Cited

U.S. PATENT DOCUMENTS

| | | | |
|---|---|---|---|
| 6,063,090 A | 5/2000 | Schlapfer | |
| 6,099,528 A | 8/2000 | Saurat | |
| 6,113,826 A | 9/2000 | Tajima et al. | |
| 6,117,173 A | 9/2000 | Taddia et al. | |
| 6,174,329 B1 | 1/2001 | Callol et al. | |
| 6,203,568 B1 | 3/2001 | Lombardi et al. | |
| 6,248,105 B1 | 6/2001 | Schlapfer et al. | |
| 6,280,442 B1 | 8/2001 | Barker et al. | |
| 6,302,630 B1 | 10/2001 | Grant | |
| 6,340,367 B1 | 1/2002 | Stinson et al. | |
| 6,342,055 B1 * | 1/2002 | Eisermann et al. | 623/17.16 |
| 6,371,957 B1 | 4/2002 | Amrein et al. | |
| 6,423,067 B1 | 7/2002 | Eisermann | |
| 6,471,705 B1 | 10/2002 | Biedermann et al. | |
| 6,565,567 B1 | 5/2003 | Haider | |
| 6,575,975 B2 | 6/2003 | Brace et al. | |
| 6,599,290 B2 * | 7/2003 | Bailey et al. | 606/86 B |
| 6,641,586 B2 | 11/2003 | Varieur | |
| 6,660,004 B2 | 12/2003 | Barker et al. | |
| 6,679,883 B2 | 1/2004 | Hawkes et al. | |
| 6,712,852 B1 | 3/2004 | Chung et al. | |
| 6,740,086 B2 | 5/2004 | Richelsoph | |
| 6,837,905 B1 | 1/2005 | Lieberman | |
| 6,974,480 B2 | 12/2005 | Messerli et al. | |
| 7,150,594 B2 | 12/2006 | Keener | |
| 7,169,150 B2 | 1/2007 | Shipp et al. | |
| 7,192,447 B2 | 3/2007 | Rhoda | |
| 7,235,079 B2 | 6/2007 | Jensen et al. | |
| 7,235,290 B2 | 6/2007 | Vallittu et al. | |
| 7,273,481 B2 * | 9/2007 | Lombardo et al. | 606/86 A |
| 7,318,825 B2 | 1/2008 | Butler et al. | |
| 7,766,942 B2 | 8/2010 | Patterson et al. | |
| 7,966,711 B2 | 6/2011 | Keener | |
| 7,988,710 B2 | 8/2011 | Jahjng et al. | |
| 7,998,180 B2 | 8/2011 | Erickson et al. | |
| 8,267,978 B2 | 9/2012 | Lindemann et al. | |
| 2002/0123751 A1 | 9/2002 | Fallin | |
| 2002/0133158 A1 | 9/2002 | Saint Martin | |
| 2003/0078583 A1 * | 4/2003 | Biedermann et al. | 606/69 |
| 2004/0034430 A1 | 2/2004 | Faiahee | |
| 2004/0127904 A1 | 7/2004 | Konieczynski et al. | |
| 2004/0143265 A1 | 7/2004 | Landry et al. | |
| 2004/0199251 A1 | 10/2004 | McCombe et al. | |
| 2004/0210226 A1 | 10/2004 | Trieu | |
| 2004/0210316 A1 * | 10/2004 | King et al. | 623/18.11 |
| 2004/0215195 A1 | 10/2004 | Shipp et al. | |
| 2004/0243129 A1 | 12/2004 | Moumene et al. | |
| 2005/0187550 A1 | 8/2005 | Grusin | |
| 2005/0187555 A1 | 8/2005 | Biedermann et al. | |
| 2005/0203516 A1 | 9/2005 | Biedermann et al. | |
| 2005/0203517 A1 | 9/2005 | Jahng et al. | |
| 2005/0203519 A1 | 9/2005 | Harms et al. | |
| 2005/0216081 A1 | 9/2005 | Taylor | |
| 2005/0228388 A1 | 10/2005 | Brodke et al. | |
| 2005/0228479 A1 | 10/2005 | Pavcnik et al. | |
| 2006/0041259 A1 | 2/2006 | Paul et al. | |
| 2006/0084986 A1 | 4/2006 | Grinberg et al. | |
| 2006/0085072 A1 | 4/2006 | Funk et al. | |
| 2006/0089644 A1 | 4/2006 | Felix | |
| 2006/0142758 A1 | 6/2006 | Petit | |
| 2006/0149228 A1 | 7/2006 | Schlapfer et al. | |
| 2006/0195093 A1 | 8/2006 | Jahng | |
| 2006/0200140 A1 | 9/2006 | Lange | |
| 2006/0235410 A1 | 10/2006 | Ralph et al. | |
| 2006/0247638 A1 | 11/2006 | Trieu et al. | |
| 2006/0276788 A1 | 12/2006 | Berry et al. | |
| 2007/0123879 A1 * | 5/2007 | Songer et al. | 606/69 |
| 2007/0156145 A1 | 7/2007 | Demakas et al. | |
| 2007/0190230 A1 | 8/2007 | Trieu et al. | |
| 2007/0233073 A1 | 10/2007 | Wisnewski et al. | |
| 2007/0250167 A1 | 10/2007 | Bray et al. | |
| 2007/0270851 A1 * | 11/2007 | Erickson et al. | 606/69 |
| 2008/0033437 A1 | 2/2008 | Shipp et al. | |
| 2008/0065070 A1 | 3/2008 | Freid et al. | |
| 2008/0077133 A1 * | 3/2008 | Schulze | 606/60 |
| 2008/0082103 A1 | 4/2008 | Hutton et al. | |
| 2008/0083613 A1 * | 4/2008 | Oi et al. | 204/237 |
| 2008/0086127 A1 | 4/2008 | Patterson et al. | |
| 2008/0086129 A1 | 4/2008 | Lindemann et al. | |
| 2008/0091214 A1 | 4/2008 | Richelsoph | |
| 2008/0097432 A1 * | 4/2008 | Schulze | 606/61 |
| 2008/0125777 A1 | 5/2008 | Veldman et al. | |
| 2008/0154367 A1 | 6/2008 | Justis et al. | |
| 2008/0243185 A1 | 10/2008 | Felix et al. | |
| 2009/0093819 A1 | 4/2009 | Joshi | |
| 2009/0093844 A1 | 4/2009 | Jackson | |
| 2009/0112265 A1 | 4/2009 | Hudgins et al. | |
| 2009/0275983 A1 | 11/2009 | Veldman et al. | |
| 2009/0326582 A1 | 12/2009 | Songer et al. | |
| 2010/0063550 A1 | 3/2010 | Felix | |
| 2010/0114167 A1 | 5/2010 | Wilcox et al. | |
| 2010/0160967 A1 | 6/2010 | Capozzoli | |
| 2012/0109207 A1 | 5/2012 | Trieu | |

FOREIGN PATENT DOCUMENTS

| | | |
|---|---|---|
| FR | 2 899 787 | 10/2007 |
| GB | 2 294 399 | 1/1996 |
| JP | 2005-270250 | 10/2005 |
| JP | 2006-187658 | 7/2006 |
| JP | 2007-307368 | 11/2007 |
| WO | WO 94/04095 A1 | 3/1994 |
| WO | WO 2007/127845 | 11/2007 |

OTHER PUBLICATIONS

S. Kawahara et al., *Clinical Imaging Diagnosis of Implant Materials for Breast Augmentation*, Ann Plast Surg., Jul. 2006; 57(1), pp. 6-12.

*VLS System Variable Locking Screw*, Interpore Cross International, 2001.

EBI Spine Systems, *EBI Ωmega21 Spinal Fixation System*, Surgical Technique, published at least as early as Sep. 1, 2006.

*Click'X Top Loading System*, Technique Guide, Synthes Spine 2003.

*Synergy IQ, Low Back Surgical Technique*, Interpore Cross International, 2003.

Office Action dated May 3, 2013, issued in U.S. Appl. No. 13/063,605, filed Mar. 11, 2011.

Office Action dated Aug. 15, 2013, issued in U.S. Appl. No. 12/557,081, filed Sep. 10, 2009.

Final Office Action dated Jun. 6, 2012, issued in U.S. Appl. No. 12/577,081, filed Sep. 10, 2009.

Office Action dated Jul. 10, 2012, issued in U.S. Appl. No. 12/208,986, filed Sep. 11, 2008.

Final Office Action dated Dec. 14, 2012, issued in U.S. Appl. No. 12/208,986, filed Sep. 11, 2008.

Office Action issued dated Feb. 16, 2013, issued in Chinese Application No. 200980144925.0, filed Sep. 11, 2011.

Office Action dated Sep. 14, 2011 issued in EP Application No. 09792417.9, filed Sep. 11, 2011.

* cited by examiner

RADIOLUCENT BONE PLATE WITH RADIOPAQUE MARKER

CROSS-REFERENCE TO RELATED APPLICATIONS

Not Applicable.

BACKGROUND OF THE INVENTION

1. The Field of the Invention

The present invention relates generally to radiolucent medical implants, and more specifically to radiolucent bone plates used to stabilize vertebrae or other bones.

2. The Relevant Technology

Bone plates are commonly used for adjusting and/or stabilizing damaged or misaligned bones in the body. For example, spinal stabilizing systems are commonly used in the surgical treatment of spinal fractures or spinal disorders such as degenerative disc disease, disc herniations, scoliosis or other curvature abnormalities. In some cases, dynamic implants are used to preserve motion between vertebral bodies. In other cases, spinal fusion is encouraged to inhibit relative motion between vertebral bodies. Often, a bone plate is used. The bone plate is attached to the exterior of adjacent vertebrae, typically with bone screws, including at a posterior, anterior, or lateral surface of the vertebrae, depending on the circumstances.

A conventional bone screw comprises a threaded shaft having a head mounted on the end thereof. The threaded shaft is inserted through an aperture on the bone plate and screwed into the vertebra. The head is sized so as to be larger than the aperture so that the head then presses against the bone plate as the shaft is screwed into the vertebra, thereby securing the vertebra to the bone plate. To be strong enough to handle the stresses placed upon them, conventional bone screws and bone plates are typically made of titanium or some other high strength, biocompatible metal. As a result of being made of metal, a physician is able to view the bone screws and bone plates using X-ray photographs during and after implantation.

However, the metal bone screws and bone plates also block the X-rays and prevent them from passing through the body. As a result, the metal bone screws and bone plates obscure adjacent bone and other X-ray viewable internal structures surrounding the area, thereby preventing the physician from viewing those structures on an X-ray photograph. This screening can limit a physician's ability to ensure proper placement/orientation of the bone screws and bone plates relative to the surrounding bone structure. Such screening can also hamper the diagnoses and treatment of problems that arise near the location of the bone screws and bone plates after the bone screws and bone plates have been implanted. These same concerns also exist anywhere in the body where a bone plate and accompanying bone screws may be inserted.

Accordingly, what is needed are bone plates that overcome some or all of the above disadvantages.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

As used in the specification and appended claims, directional terms, such as "top," "bottom," "up," "down," "upper," "lower," and the like are used herein solely to indicate relative directions in viewing the drawings and are not intended to limit the scope of the claims in any way.

Figure 1:
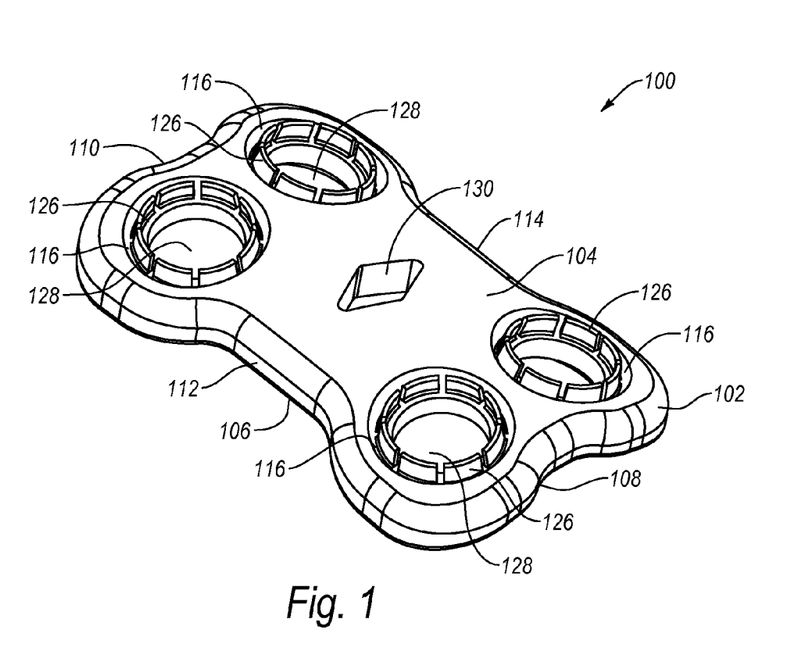
FIG. 1 is a top perspective view of a bone plate according to one embodiment of the present invention.
Figure 2:
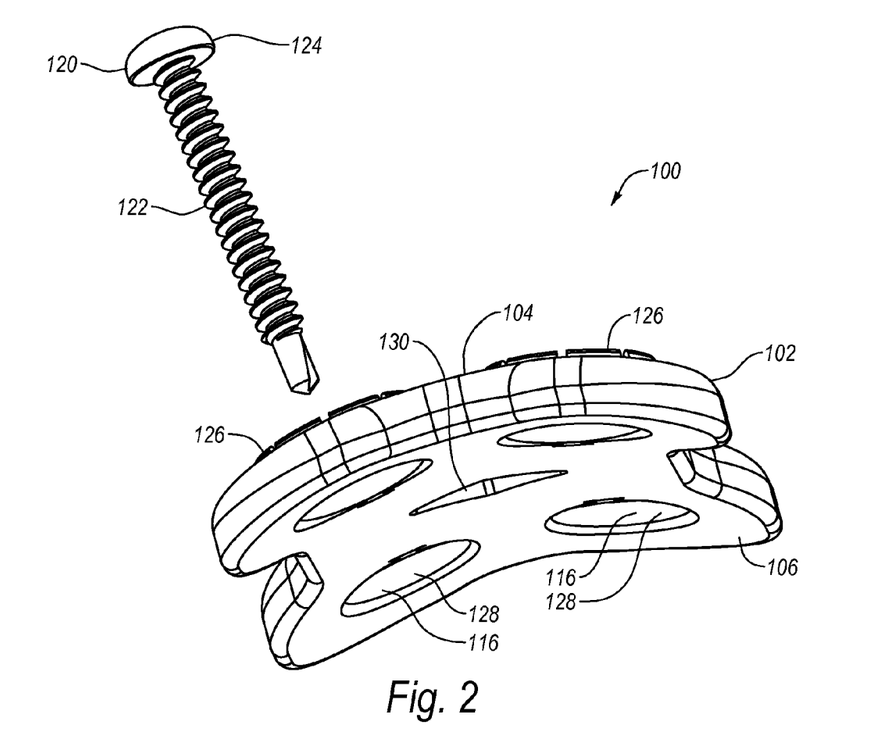
FIG. 2 is bottom perspective view of the bone plate shown in FIG. 1 along with a corresponding bone screw.

Depicted in FIGS. 1 and 2 is one embodiment of a bone plate 100 incorporating features of the present invention. Bone plate 100 is designed to be used for stabilizing two adjacent vertebrae of a spine as part of a procedure for fusing together the adjacent vertebrae. Bone plate 100 can also be used for stabilizing a series of consecutive vertebrae for manipulation of the spine to correct spinal deformities such as scoliosis. It is appreciated that bone plate 100 and/or discrete elements thereof can also be used in other procedures for anchoring, manipulating, and/or stabilizing various bones.

Bone plate 100 comprises a main body 102 having a top surface 104 and an opposing bottom surface 106 that extend longitudinally from a proximal end 108 to a spaced apart distal end 110. Top and bottom surfaces 104 and 106 also extend laterally from a first side 112 to a spaced apart second side 114. Main body 102 can be curved in one or more directions, as shown in the depicted embodiment, or can be substantially planar.

A plurality of apertures 116 are formed in main body 102 that extend completely through main body 102 between top surface 104 and bottom surface 106. Each aperture 116 is designed so that the shaft 122 of a bone screw 120 can be inserted therethrough, as shown in FIG. 2, while the head 124 of the bone screw 120 is prevented from doing so.

Bone screw 120 is threaded into a vertebra while head 124 biases against bone plate 100 so as to rigidly attach the vertebra to bone plate 100. In some embodiments, an insert 126, as discussed in more detail below, is positioned within each aperture 116 to provide a surface for the head 124 of the bone screw 120 to press against and, in some cases, to provide a means for preventing bone screw 120 from "backing out" after bone screw 120 has been inserted into the vertebra. Each insert 126 has a passageway 128 that aligns with the aperture 116 through which bone screw 120 can pass.

Other apertures can also be included in main body 102 to aid the physician in implanting the bone plate within the body. For example, in the depicted embodiment a viewing aperture 130 that passes completely through main body 102 is positioned generally centrally on the main body 102 so as to allow the physician to view the underlying spine when installing the bone plate 100. The number of viewing apertures 130 can vary. For example, in one embodiment, a single viewing aperture 130 is positioned on main body 102. In other embodiments, a plurality of viewing apertures 130 are incorporated (see, e.g., FIG. 5). In other embodiments, viewing apertures 130 are omitted altogether.

Figure 3:
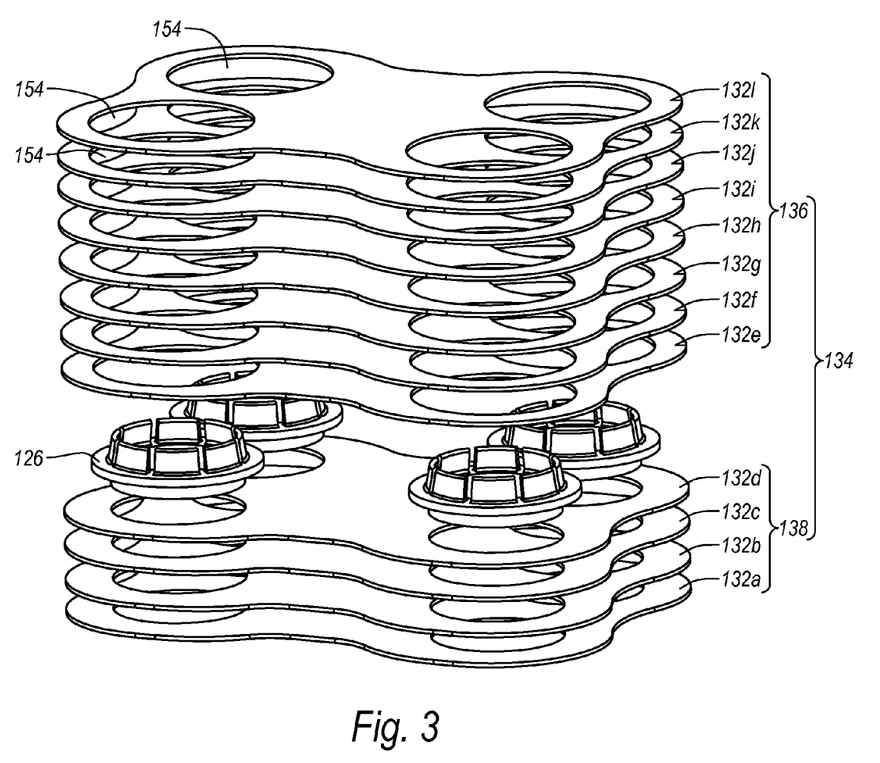
FIG. 3 is a perspective view of the bone plate shown in FIG. 1 in an early stage of manufacture, showing the separate layers and insert before being bonded together.

As shown in FIG. 3, main body 102 is comprised of a plurality of separate layers 132a through 132l that are bonded together as described in more detail below. As shown, the layers 132 are positioned on top of each other so as to form a stack 134. If inserts 126 are used, such as in the depicted embodiment, stack 134 can be divided into an upper stack 136 and a lower stack 138, with insert 126 being positioned between upper and lower stacks 136 and 138. For example, in the depicted embodiment, upper stack 136 comprises layers 132a-132d, and lower stack 138 comprises layers 132e-132l. The number of layers 132 used in main body 102 can vary, depending on various factors, such as the thickness of each layer, the desired length and width of main body 102, and the desired overall strength of main body 102. In one embodiment, the number of layers 132 that make up stack 134 is between 2 to 100, with 2 to 20 being common. Other numbers of layers 132 can also be used.

Figure 4:
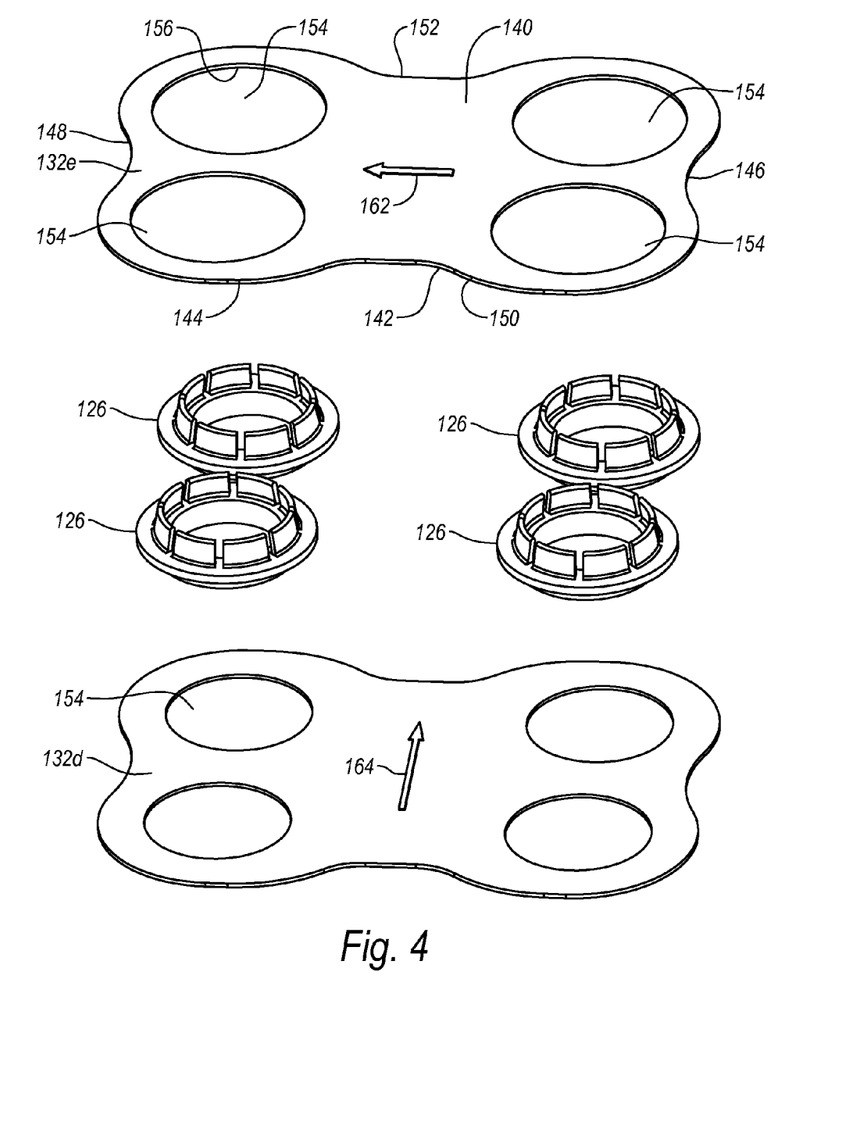
FIG. 4 is a perspective view of the insert and a couple of layers shown in FIG. 3.

All of the layers 132 in the upper and lower stacks 136 and 138 can have the same general structure, except where noted. In light of this, FIG. 4 depicts inserts 126 and only the layers 132d and 132e that adjoin inserts 126 so as to provide clarity in the discussion of the structural elements. Each layer 132 has a top surface 140 and an opposing bottom surface 142 with a perimeter sidewall 144 extending therebetween. Top and bottom surfaces 140 and 142 both extend longitudinally from a first end 146 to a spaced apart second end 148. Top and bottom surfaces 146 and 148 also extend laterally from a first side 150 to a spaced apart second side 152. As shown in the depicted embodiment, top and bottom surfaces 140 and 142 are generally parallel to each other and substantially planar. However, in other embodiments top and bottom surfaces 140 and 142 can be non-parallel and/or curved if desired. In addition, each layer 132 can be substantially rectangular when viewed face-on (see, e.g., FIG. 13) or can have a curved outer edge 144, as in the embodiment depicted in FIG. 4, depending on the desired shape.

As noted above, main body 102 has apertures 116 (see FIG. 1) formed therein that allow bone screws to pass therethrough. These apertures can be formed in each layer 132 before the layers are bonded together, or can be formed in main body 102 after the layers have been bonded. For those embodiments in which apertures 116 are formed before bonding, each layer 132 has formed therein a plurality of apertures 154 that, when aligned with apertures 154 on the other layers 132, forms apertures 116 of main body 102 when the layers are bonded together. Each aperture 154 extends all the way through layer 132 between the top and bottom surfaces 140 and 142 and is bounded by an encircling sidewall 156 extending through the layer 132.

As noted above, apertures 116 are sized and positioned on main body 102 so that a bone screw can be inserted therethrough when the layers 132 are positioned in the stack 134. In addition, if an insert 126 is used, the apertures 116 are sized to also receive the insert 126. As such, the apertures 154 of each layer 132 are aligned with each other, as shown in FIG. 3. Note that although the apertures 154 are aligned, the size of the apertures 154 may vary between layers 132 (see, e.g., FIG. 11).

The number of apertures 154 formed on each layer 132 depends on the number of vertebrae that the bone plate is designed to span; for each vertebra in the span, a pair of apertures 116 is included in bone plate 100, laterally aligned with each other. For example, bone plate 100 shown in FIG. 1 is configured to fuse two adjacent vertebrae together. As such, each layer 132 has two pairs of apertures 154, as shown in FIG. 4, one pair corresponding to one of the vertebrae and the other pair corresponding to the other vertebra.

Figure 5:
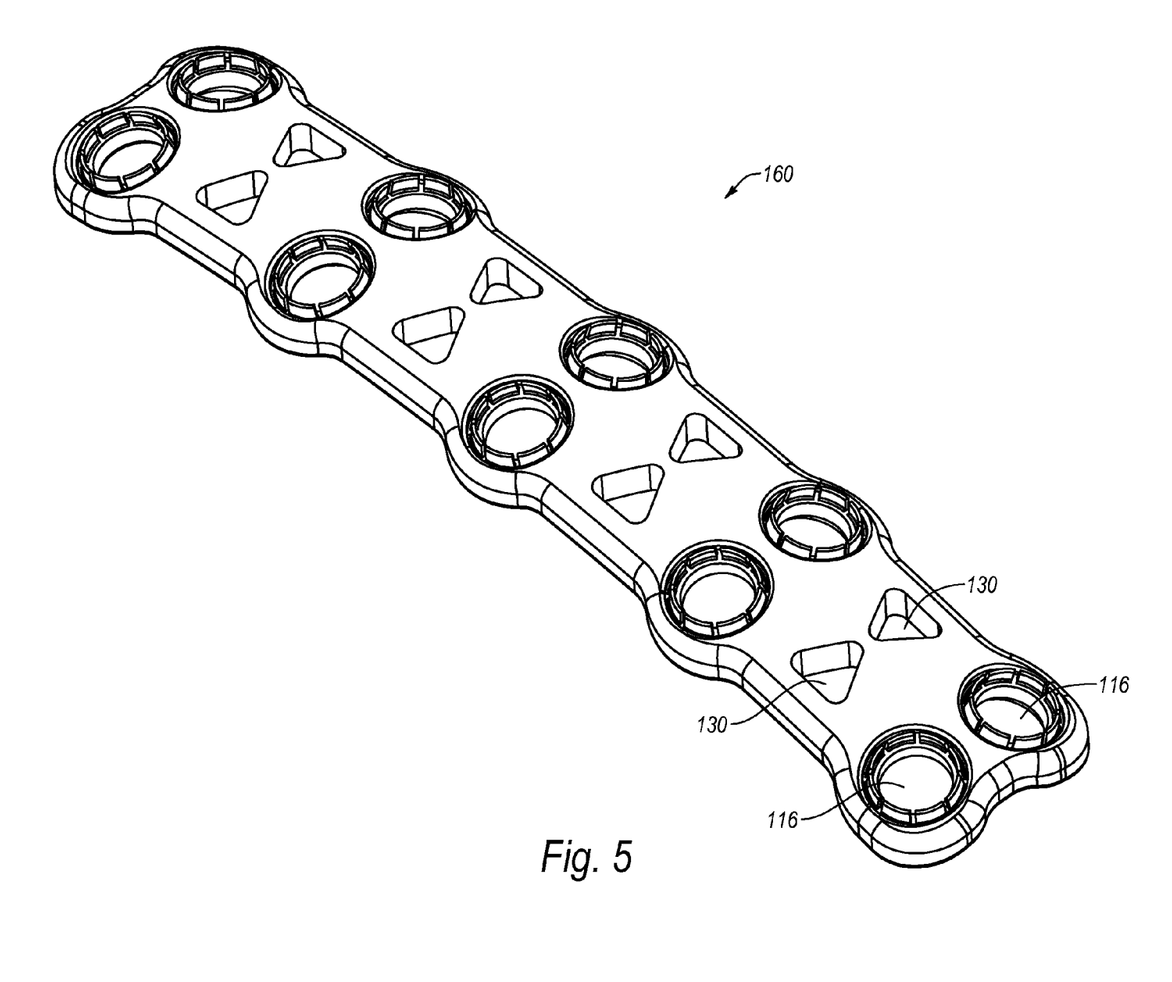
FIG. 5 is a perspective view of a bone plate configured to span five vertebra according to one embodiment.

Of course, in embodiments in which the bone plate is designed to span more than two vertebrae, more than four apertures 116 can be formed therein. For example, bone plates that are designed to span 3, 4, 5, 6, 7, or even 8 vertebrae can respectively have 6, 8, 10, 12, 14, and 16 apertures formed on each layer. FIG. 5 depicts one embodiment of a bone plate 160 designed to span five vertebrae and thus having ten apertures 116 formed therein.

Figure 16:
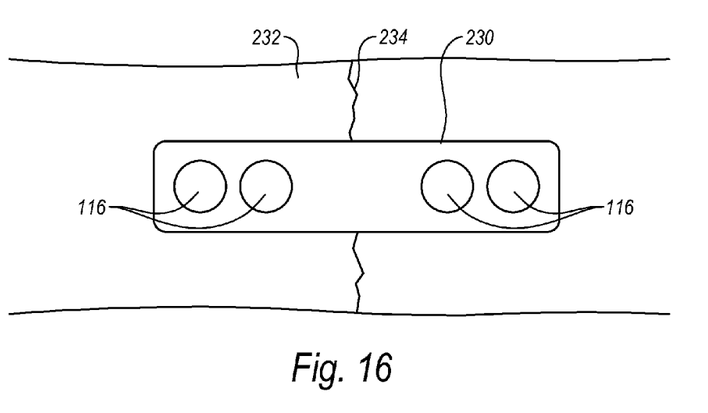
FIG. 16 is a top view of a bone plate positioned to span a bone fracture according to one embodiment.

For bone plates used to anchor, manipulate, and/or stabilize other bones in the body, the number of apertures and positions on the layer can vary. For example, FIG. 16 depicts one embodiment of a bone plate 230 designed to attach to two sections of a bone 232 on either side of a bone fracture 234. In bone plate 230, four separate apertures 116 are formed that are all aligned in a row. Apertures 116 are positioned so that when bone plate 230 is used, two of the apertures 116 will be positioned on either side of fracture 234, as shown. Other aperture orientations and configurations can also be used based on the intended use of the bone plate.

Each layer 132 is generally comprised of a radiolucent material that allows viewing of adjacent bone or other internal structures on an X-ray photograph that are in the viewing path of bone plate 100. Using radiolucent material for each layer 132 also minimizes scattering caused by commonly used metals in X-Rays, CAT scans, MRI's, and other types of imaging systems.

One example of a radiolucent material that can be used in each layer 132 is a radiolucent biocompatible fiber and adhesive matrix, such as, e.g., a carbon fiber/epoxy tape. In this embodiment, an adhesive is applied to one or more elongated biocompatible fibers that are then allowed to partially cure. The fibers can comprise individual fibers or multiple fibers in a fiber bundle or tow. The layers 132 can be individually formed from such a matrix. Alternatively, a large sheet of such a matrix can be formed and a plurality of layers 132 can be cut out of the large sheet. Methods of manufacturing the bone plate 100 are discussed in more detail below.

Many different types of biocompatible fibers and adhesives can be used to form each layer 132. For example, the fibers can be comprised of carbon, fiberglass, poly paraphenylene terephthalamide (PPTA, more commonly known as Kevlar®), other aramids, and ceramics. Other radiolucent, biocompatible fibers having desired properties can also be used.

Although fibers having multiple different properties can be used, typical fibers have a diameter in a range between about 5 microns to about 18 microns with about 5 microns to about 7 microns being more common and a tensile strength in a range between about 300 ksi to about 1000 ksi with about 600 ksi to about 1000 ksi being more common. Other diameters and tensile strengths can be used. The fibers can be sized or unsized. By "unsized," it is meant that the fibers have not been coated with a material to improve adhesion of the resin or adhesive. If the fibers are sized, biocompatibility of the sizing needs to be considered.

For each particular layer 132, the fibers that make up the layer can be oriented in differing directions (i.e., bidirectional) or generally oriented in the same direction (i.e., unidirectional). For example, all of the fibers in layer 132e shown in FIG. 4 can be oriented in the direction shown by arrow 162, and is thus a unidirectional layer. As is known in the art, this causes the layer to be very rigid in the direction 162 in which the fibers are oriented, while being flexible in a direction orthogonal to the direction of the fibers.

If desired, each layer 132 may be formed so that the fibers that make up the layer are oriented in a direction that is different from the direction of the fibers forming other layers. For example, all of the fibers in layer 132d shown in FIG. 4 can be oriented in the direction shown by arrow 164, which is a different direction than the direction 162 of the fibers of layer 132e, discussed above.

As a result of the differing directions of the layers' fibers, each layer 132 may impose a stiffness and flexibility in different directions than other adjoining layers 132. When the layers 132 are bonded together, this can result in the resulting bone plate 100 having a unique flexibility/rigidity combination. Because of the number of layers 132 that make up the main body 102 of bone plate 100, an almost infinite combination of layer fiber directions can be obtained. As such, bone plate 100 can be manufactured based on the unique requirements of each patient. In this way, depending on the orientation of each of the layers 132, the main body 102 of bone plate 100 can be designed to impart maximum stiffness in one direction and maximum flexibility in another direction, or can have an overall consistent stiffness/flexibility combination in all directions, or can be any combination thereof. If desired, the main body 102 of bone plate 100 can be formed so as to have approximately the same modulus of elasticity as the bones to which bone plate is to be attached. Also, the layers 132 of the main body 102 can be formed so as to allow dynamic stabilization to occur, thereby preventing potentially harmful stress shielding that typically occurs with conventional bone plates.

Examples of biocompatible adhesives that can be used with the fibers include polyester, vinylester, and epoxy resins, as well as other molten plastics. Exemplary biocompatible epoxies that can be used to bond the fibers include the Master Bond Inc. epoxies EP42HT-2 and EP45HT MED and the Epotek epoxies 301-2 and 375. Examples of biocompatible resins that can be used to bond the fibers include polyetheretherketone (PEEK), polyethylene, polyurethane, polyimide, polyamide, and polyaryletherketone (PAEK). Other epoxies or resins that are implantable, biocompatible, sterilizable, and have the desired strength properties can also be used.

The thickness of each layer 132, defined as the distance between the top and bottom surfaces 140 and 142 thereof, depends on the types of materials used, the size of the materials, and the amount of material used. The thickness of each layer is typically between about 0.1 mm to about 2 mm, with between about 0.1 mm to about 0.5 mm being common. Other thicknesses can also be used. In addition, the thicknesses of all of the layers 132 can be substantially the same or the thicknesses of each layer can vary from the other layers.

In some embodiments, one or more radiopaque positioning markers are used with the present invention. Such markers can further aid in the implantation and positioning of the bone plate as these markers are viewable on X-Ray photographs. The positioning markers can be placed between layers, be positioned on a surface of the layer, or be embedded within the layer, or comprise any combination thereof.

Figure 6:
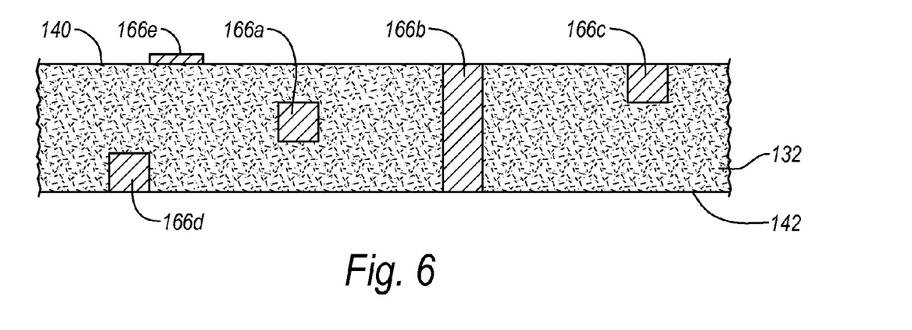
FIG. 6 is a cross-sectional side view of a portion of a layer according to one embodiment having a plurality of radiolucent markers disposed therein.

One example of a positioning marker is a radiopaque marker disposed within or on a layer. For example, FIG. 6 shows an embodiment of a layer 132 in which a number of biocompatible positioning markers 166 are embedded within the layer. In the depicted embodiment, one positioning marker 166a is completely disposed within the layer. Another positioning marker 166b is positioned within layer 132 so as to pass completely through layer 132 between top and bottom surfaces 140 and 142. Still other positioning markers can be used that are exposed on the top or the bottom surfaces, such as positioning markers 166c and 166d, respectively. Exposed positioning markers can alternatively be positioned on the surface of layer 132, such as positioning marker 166e, which is positioned on top surface 140. Other arrangements are also possible. Each type of positioning marker 166 shown in FIG. 6 can be used alone or in combination with one or more of the other types of positioning markers.

As noted above, positioning markers 166 are comprised of a radiopaque material so as to be viewable on an X-ray photograph. As such, positioning markers 166 can be comprised of metal foils, meshes, wires, plates and powders such as tungsten, tantalum, gold, platinum, iridium or barium (sulfate). During implantation and positioning of bone plate 100, the X-ray image of positioning markers 166 can help the physician determine the position and orientation of bone plate 100.

In one embodiment, a positioning marker 166 is positioned about midway between proximal end 108 and distal end 110 of bone plate 100. In other embodiments, a positioning marker 166 is positioned substantially closer to proximal end 108 or distal end 110 or at any desired location. In other embodiments, such as that shown in FIG. 6, it is appreciated that two or more positioning markers 166 can be positioned along bone plate 100 at spaced apart locations.

Figure 7:
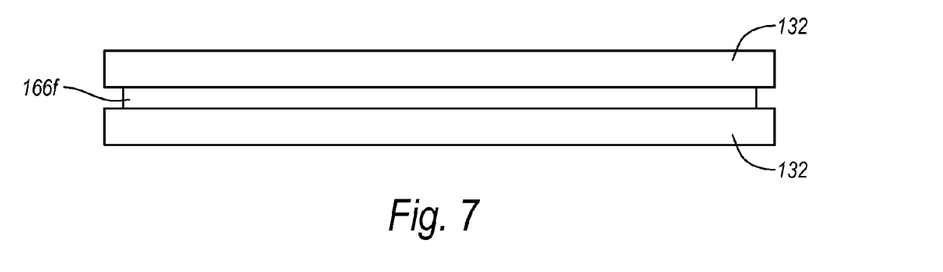
FIG. 7 is a side view of a positioning marker being disposed between two layers according to one embodiment.

One example of a positioning marker 166 that is placed between layers 132 is shown in FIG. 7. Positioning marker 166f essentially is another layer in the stack 134 and can be sized so as to cover the same area as layers 132 or just a portion thereof. Also, depending on the amount of X-Ray viewability desired, positioning marker 166f can comprise a solid material, a mesh-type of arrangement, or a powdery layer, comprised of any of those materials discussed above. Other types of positioning marker arrangements can also be used. Furthermore, positioning marker 166f can be used by itself or in combination with one or more of the positioning markers 166 shown in FIG. 6.

Figure 8:
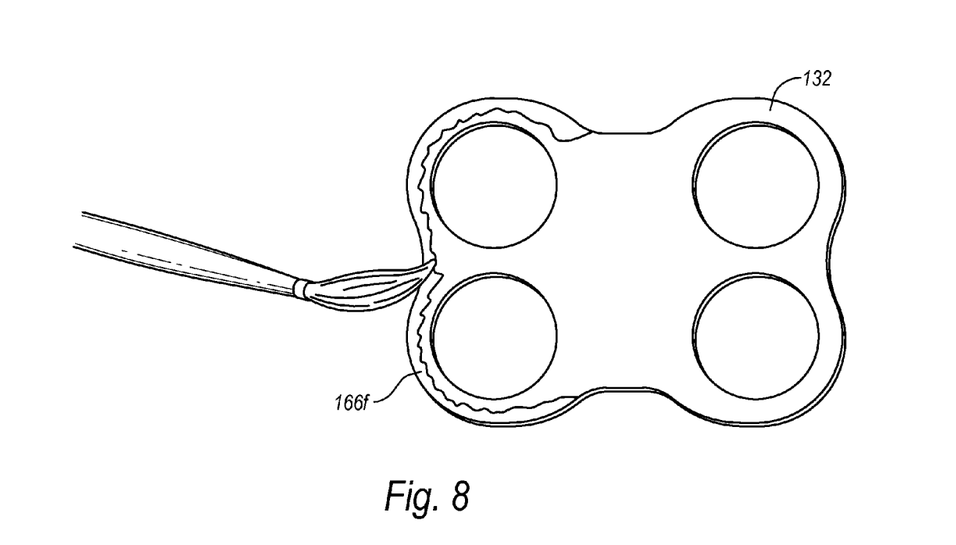
FIG. 8 is a perspective view of a layer according to one embodiment having a radiolucent marker painted thereon.

Depicted in FIG. 8 is another embodiment of a positioning marker 166f. Positioning marker 166f is again comprised of a radiopaque material but in this embodiment is in the form of paint or ink that is painted or printed onto top surface 140 of one of the layers 132. It is appreciated that, alternatively, positioning marker 166f can be painted or printed on to one of the other surfaces of any of the layers 132. Positioning marker 166f can be used in place of or in combination with one or more additional positioning markers 166 discussed above. Positioning marker 166f can form a continuous perimeter that encircles the outer edges of the layer 132 so as to form an outline thereof or can be any other type of configuration.

In other embodiments, pieces of radiopaque material can be embedded within the matrix as radiopaque positioning markers 166. These pieces can comprise small or large particles that are placed within the matrix during manufacture either randomly or in a particular pattern. One example of an embedded radiopaque material is a metal powder that is mixed with one or more of the layers 132. Many different shapes and patterns can be used for these radiopaque positioning markers. Also, these pieces of radiopaque material can be used with or without any of the other types of positioning markers 166 discussed above.

It is appreciated that radiopaque markers can be any desired shape and be located at any position or orientation that will produce a desired marking. It is also appreciated that inserts 102 can also be used as positioning markers, if made of radiopaque material. Other configurations are also possible.

Figure 9:
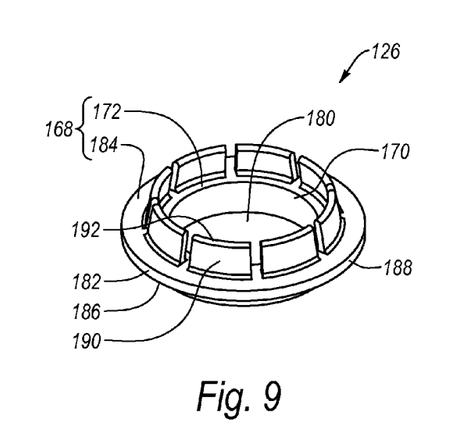
FIGS. 9 and 10 are top and bottom perspective views, respectively, of the insert shown in FIG. 4.
Figure 10:
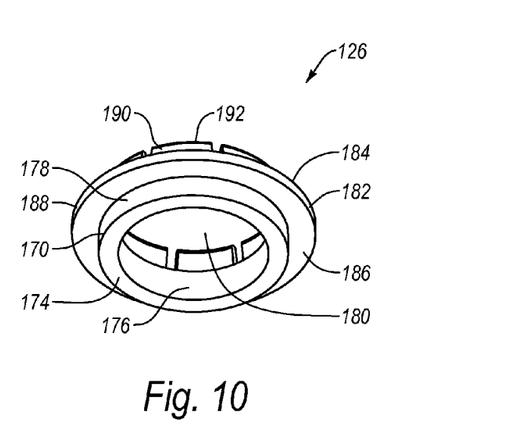

As noted above, inserts 126 can be used to provide a biasing surface 168 for the bone screws 120 and/or to provide a means for preventing the bone screw from backing out once inserted into the vertebra. Turning to FIGS. 9 and 10, each insert 126 comprises an annular main body 170 having a top surface 172 and an opposing bottom surface 174 with perimeter inner and outer side surfaces 176 and 178 extending therebetween. The inner side surface 176 bounds a passageway 180 that extends completely through the main body 170 between top surface and bottom surfaces 172 and 174.

An annular flange 182 having a top surface 184 and an opposing bottom surface 186 extends radially outward from outer side surface 178 of main body 170 to an outer perimeter surface 188. The top surface 184 of flange 182 can be coplanar with the top surface 172 of main body 170. As such, the biasing surface 168 of the insert 126 can comprise the top surface 172 of main body 170 and the top surface 184 of flange 182. Although flange 182 is depicted as a continuous annular flange, this is not required. In some embodiments, gaps can be included between flange sections. For example, flange 182 can be comprised of two or more flange sections that radiate out from main body 170. The flange sections can be equally spaced around main body 170, or can be irregularly spaced. Also, each flange section can be the same size or different sizes. Other flange configurations are also possible.

The inner diameter of the passageway 180 of main body 102 is sized so that bone screw 120 can pass therethrough while the head 124 thereof contacts and biases against the biasing surface 168. Inserts 126 can be comprised of titanium, stainless steel, or other high strength, biocompatible material.

In some embodiments, insert 126 also includes means for preventing the bone screw from backing out of the vertebra. For example, in the depicted embodiment, radially encircling passageway 180 and extending upward (i.e., axially) from the top surface 168 of insert 126 is a plurality of fingers 190 that act as a screw locking mechanism. Each finger 190 extends from the top surface 168 of insert 126 to a distal end 192. Each finger 190 leans radially inward so that the head 124 of bone screw 120 will be retained therein. That is, the distal end 192 of each finger 190 is positioned closer to the longitudinal axis of the aperture. The fingers 190 are flexible so that when bone screw 120 is inserted through insert 126 and threaded into a vertebra, the head 124 of bone screw 120 causes distal end 192 of each finger 190 to flex outward as it passes thereby. Once head 124 is past the distal ends 192 of fingers 190, the head 124 of the bone screw 120 becomes positioned adjacent to biasing surface 168 of insert 126. In addition, the distal ends 192 flex back inward so that the fingers 190 bias against the head 124 of bone screw 120. As a result, fingers 190 retain bone screw 120 in this position. Other means for preventing bone screw 120 from backing out of the vertebra, as is known in the art, can alternatively be used. It is also appreciated that other types of inserts can alternatively be used in embodiments of the present invention, as is known in the art.

To manufacture bone plate 100, the desired number of radiolucent layers 132 are formed as discussed previously, with or without apertures 154. If desired, one or more radiopaque positioning markers 166 are positioned in or on one or more of layers 132 as the layers are formed. Layers 132 are then aligned and stacked on top of each other to form stack 134. If apertures 154 have been formed in the individual layers 132, the apertures 154 of layers 132 align with each other in stack 134. Layers 132 can be stacked so that the fibers of different layers are all oriented in the same direction or aligned in different directions.

Figure 11:
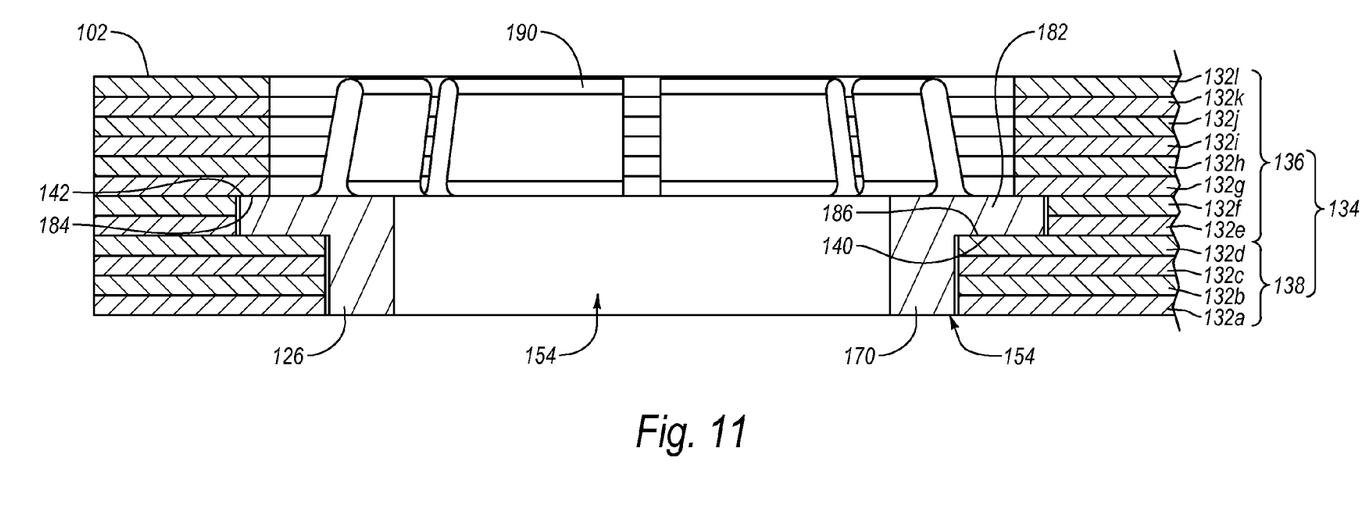
FIG. 11 is a cross-sectional side view of a portion of a bone plate according to one embodiment showing the positioning of the stacked layers and insert.

If insert 126 is used, the insert can be positioned within stack 134 between the upper and lower stacks 136 and 138 as the layers 132 are being stacked. For example, as shown in FIG. 11 the layers 132a-132d that form the lower stack 138 are aligned and stacked first, then the insert 126 is positioned on the top layer 132d of the lower stack 138. When positioned thusly, main body 170 extends down through apertures 154 of one or more of the layers 132 of lower stack 138 while bottom surface 186 of flange 182 rests on the top surface 140 of the topmost layer 132d of lower stack 138. The rest of the layers 132e-132l are then stacked onto layer 132d of lower stack 138 to form upper stack 136.

As shown in the depicted embodiment, one or more layers 132 of upper stack 136 may have apertures 154 that are large enough so as to receive the flanges 182 therein (see, e.g., layers 132e and 132f in FIG. 11). At least one of the layers 132 of upper stack 136 has apertures 154 with a smaller diameter than the flange 182 of insert 126 (see, e.g., layers 132g-132l in FIG. 11). The lowermost of these layers (layer 132g) is positioned above insert 126 so that the bottom surface 142 of that layer rests on the top surface 184 of flange 182. The rest of the layers 132 of upper stack 136 are then stacked on top of the layer 132g so as to complete upper stack 136, as shown in FIG. 11.

By stacking layers 132 and insert 126 in this manner, the overlapping of the layers 132 with flange 182 rigidly secures insert 126 in place once stack 134 has been cured. Furthermore, fingers 190, if used, are positioned within apertures 154 of layers 132 of upper stack 136. Although not required, to receive fingers 190, the diameters of apertures 154 in the layers of the upper stack 136 are typically larger than the diameters of the apertures 154 in the layers of the lower stack 138.

Figure 12:
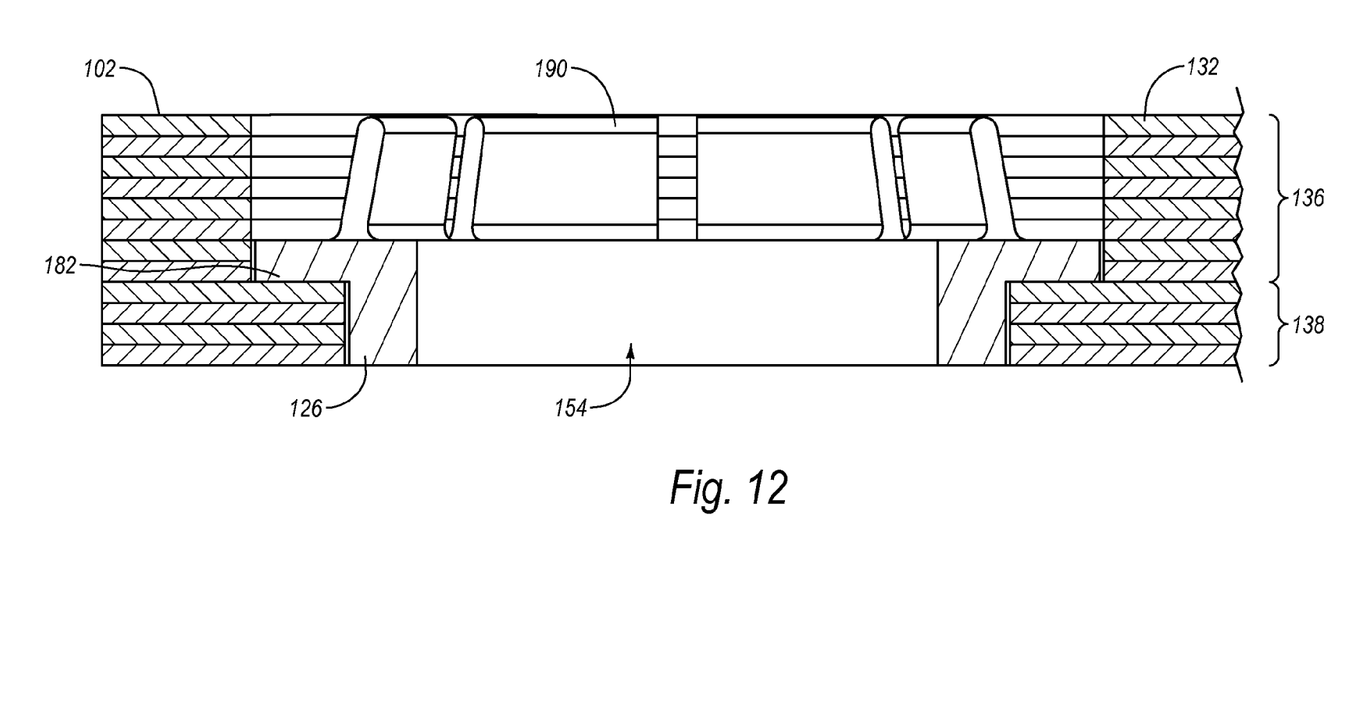
FIG. 12 is a cross-sectional side view of a portion of another bone plate according to one embodiment showing the positioning of the stacked layers and insert.

In some embodiments, bone plate 100 is designed so that layers 132 do not overlap flange 182, such as in the embodiment shown in FIG. 12. In those embodiments, insert 126 can be positioned while the layers 132 are being stacked, as discussed above, or can be placed into the apertures 154 after stack 134 has already been completely stacked.

Alternatively, the insert 126 can be positioned within the main body 102 after the layers 132 have been molded and cured if the layers 132 do not overlap the flange 182. In those cases, the apertures 154 can be omitted from the individual layers 132 and the apertures 116 can instead be drilled into main body 102 after stack 134 has been molded and cured. Where insert 126 and layers 132 of upper stack 136 do not overlap, the insert 126 is secured to the main body 102 by adhesive, press fit, or other known securing means.

It is also appreciated that in embodiments that do not include inserts, the apertures 154 can likewise be omitted from individual layers 132 and drilled into main body 102 as discussed above after the stack 134 has been molded and cured.

Figure 13:
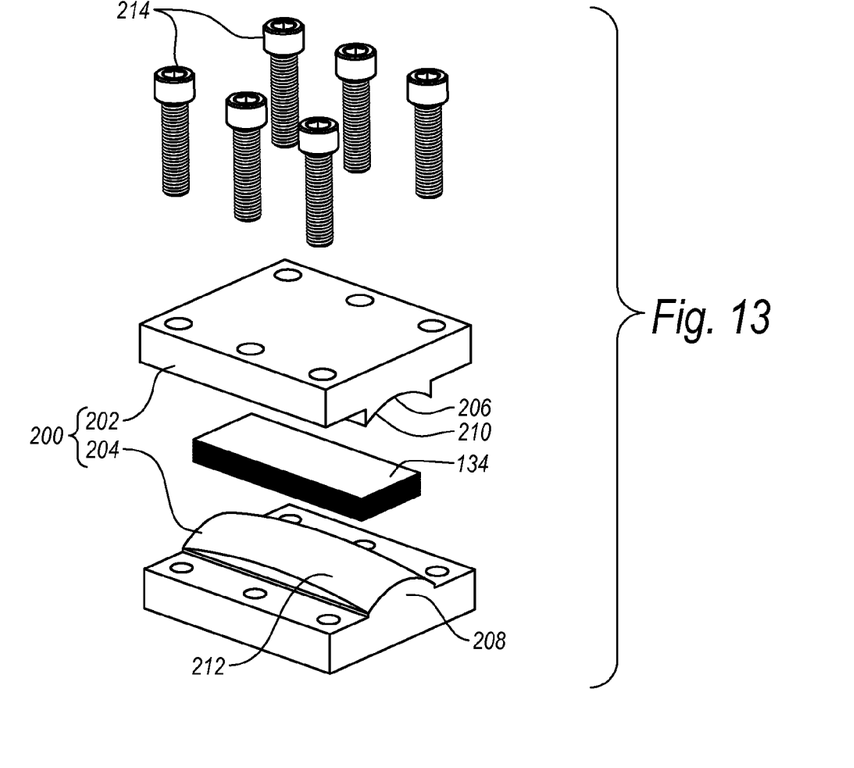
FIGS. 13 and 14 are perspective views of a mold according to one embodiment into which the bone plate has been inserted to be formed.
Figure 14:
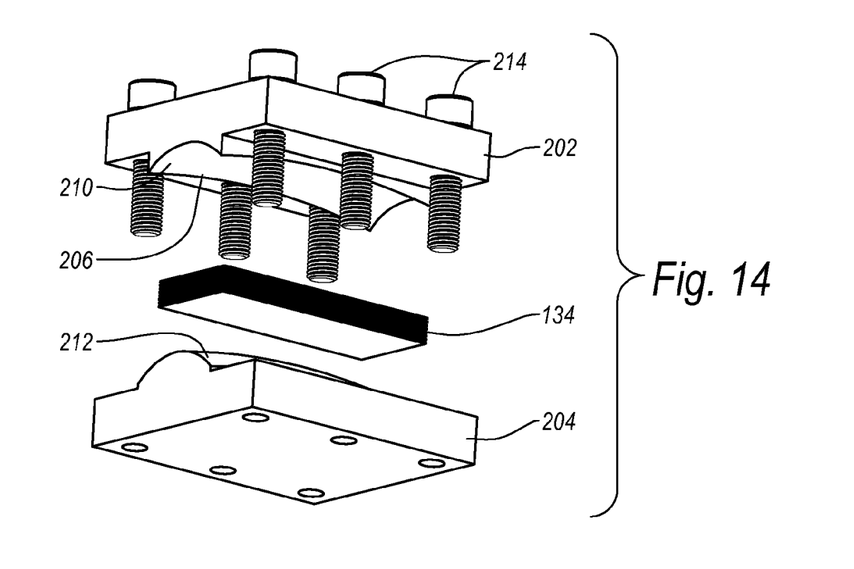

After stack 134 has been assembled, with or without inserts disposed therein, the stack 134 is then placed into a mold 200, as depicted in FIGS. 13 and 14, and shaped and cured therein. Mold 200 comprises an upper plate 202 and a lower plate 204 designed to compress stack 134 therebetween and thereby mold stack 134 into a desired shape as the stack is being cured. To accomplish this, upper and lower plates 202 and 204 have mating molding sections 206 and 208 shaped to match the desired final shape of the cured main body 102. For example, in the depicted embodiment, the molding section 206 of upper plate 202 has a surface 210 that is curved in a convex manner both longitudinally and laterally, while molding section 208 of lower plate 204 has a mating compound concave surface 212. When pressed together the surfaces 210 and 212 of the molding sections 206 and 208 align with each other.

Stack 134 is placed between molding sections 206 and 208 of upper and lower plates 202 and 204, and upper and lower plates 202 and 204 are then pressed together. This causes stack 134 to be firmly pressed between molding sections 206 and 208 and to take the shape formed by the surfaces 210 and 212 of the molding sections. In the depicted embodiment, a plurality of screws 214 are used to create the force necessary to press the upper and lower plates 202 and 204 together. Other methods of pressing upper and lower plates 202 and 204 together can alternatively be used, as is known in the art. For example, a conventional press, clamps, weights, or other means or methods can be used.

Once positioned within the pressing mold 200, stack 134 is left for a specific period of time to allow the stack to cure. Once the curing time period has elapsed, stack 134, which now forms the molded main body 102, is removed from mold 200. The main body 102 now has a curvature that matches the curves on the molding sections 206 and 208, such as is shown in FIGS. 1 and 2.

Once cured, any machining of main body 102, if necessary, can be done. For example, main body 102 can be shaped as desired. In addition, the edges of main body 102 can be machined so as to be smooth and to get rid of any rough edges. Furthermore, holes or other apertures 130 can be formed within the main body at this time. For example, as shown in FIG. 1, one or more holes 130 are formed that will aid the physician when positioning the bone plate.

In addition, in embodiments that do not have inserts, or in which inserts are to be inserted into the apertures after molding, the apertures 116 can be drilled through the cured main body 102 at this time. In those embodiments, the apertures 116 are usually counter sunk into the main body 102 to match the shape of the insert 126 (if used) or to provide a ledge that bone screw 120 can press against (if an insert is not used) when the bone screw is screwed into the vertebra.

If not already secured within apertures 116, the inserts 126, if used, are then inserted into apertures 116 and secured in place by adhesive, press fit, fastener, or other means known in the art. When cured and completed, bone plate 100 can receive bone screws 120 within apertures 116.

Figure 15:
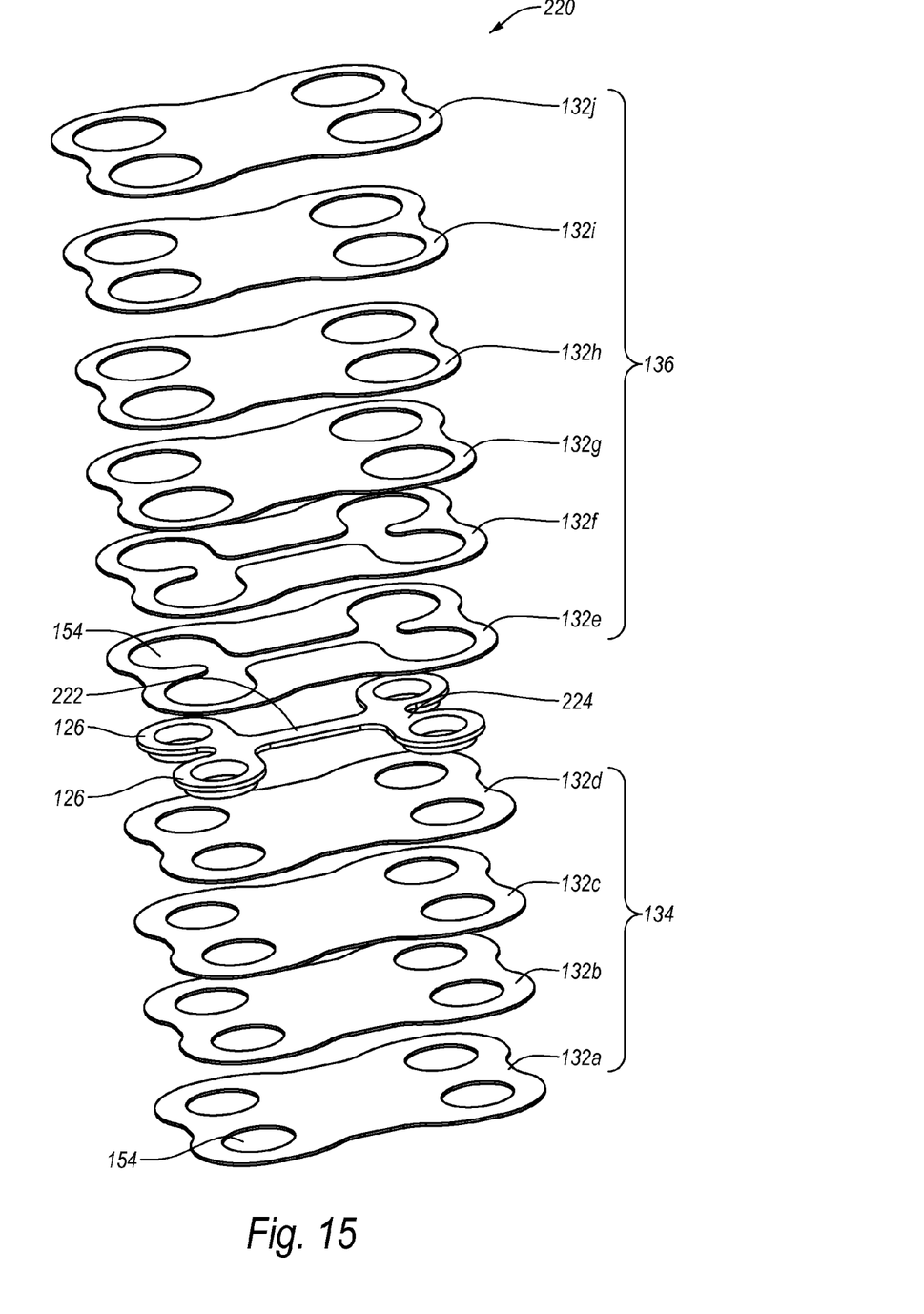
FIG. 15 is an alternative bone plate according to another embodiment of the present invention.

FIG. 15 depicts an alternative embodiment of a bone plate 220 before the layers 132 are molded and cured. Similar to bone plate 100, bone plate 220 comprises a number of layers 132 stacked so as to form upper and lower stack 136 and 138, each layer 132 having a plurality of apertures 154. Bone plate 220 also includes inserts 126 positioned in each aperture 154. However, in bone plate 220, inserts 126 are integrally connected via a connecting portion 222 so as to form a single unitary insert 224 that includes all of the inserts 126. This unitary construction provides the added benefit of lateral strength between the inserts 126. It also allows the connecting portion 222 to be used as a positioning marker, if desired. Because of the inclusion of connecting portion 222, the apertures 154 of one or more layers 132 in the upper stack 136 are formed so as to receive those portions therein (see, e.g., layers 132e' and 132f). In the depicted embodiment, insert 224 is positioned between upper and lower stacks 136 and 138 before curing so that connecting portion 222 will be able to be positioned between upper and lower stacks 136 and 138. Applicant notes that in the depicted embodiment, insert 224 does not include means for preventing the bone screw from backing out of the vertebra, although such means can be included, if desired.

Most traditional bone screws 120 can be used with the present invention. It is also appreciated that one or more of the bone screws 120 can incorporate radiolucent material, if desired. For example, bone screws according to those disclosed in U.S. patent application Ser. No. 12/208,986, filed on Sep. 11, 2008, which is incorporated herein by specific reference, can also be used with the present invention, adapted and modified as necessary.

A number of different methods and embodiments have been disclosed herein. It is appreciated that the different methods and components from the different embodiments can be mixed and matched to produce a variety of still other different embodiments. Furthermore, although the bone plates discussed herein have been described in relation to their use in fusing together adjacent vertebrae, it is appreciated that this is exemplary only. That is, bone plates according to the present invention can also be used to fuse or otherwise connect other types of adjacent bones. For example, a bone plate according to the present invention can be used for cranial fusing. Other bone fusing can also be accomplished using embodiments of the present invention. For example, FIG. 16 shows one embodiment of a bone plate used to aid in fusing a broken bone at a fracture point, as discussed above. Other uses are also possible.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A bone plate comprising:
   a main body configured to position adjacent bones with respect to each other, the main body comprising a plurality of separate layers bonded together, each layer being comprised of a radiolucent material and having a first aperture extending through the layer, the plurality of separate layers being stacked such that the first apertures of all of the layers are aligned with each other so as to form a first body aperture extending through the main body, a spaced apart second body aperture also extends through the main body;
   an insert bounding a passageway extending therethrough and including an outwardly extending flange, the insert being at least partially disposed within the aligned first apertures so that the flange is disposed directly between two of the plurality of separate layers, the plurality of separate layers being compression molded together so that the separate layers are directly bonded consecutively to each other and the two of the plurality of separate layers are directly bonded to the flange so that the flange is rigidly fixed to the main body; and
   the plurality of separate layers comprising:

a plurality of separate first layers each having the first aperture that are aligned, the plurality of separate first layers being disposed on a first side of the flange of the insert;

a plurality of separate second layers each having the first aperture that are aligned, the plurality of separate second layers being disposed on an opposing second side of the flange of the insert; and a first middle layer disposed between the first layers and the second layers, the first middle layer having the first aperture extending therethrough, the first aperture of the first middle layer encircling an outer perimeter edge of the flange of the insert so that the first middle layer does not overlay the flange, wherein the first layers are directly bonded consecutively together, the second layers are directly bonded consecutively together and the first middle layer is directly bonded to one of the first layers or one of the second layers.

2. The bone plate as recited in claim 1, wherein the main body extends longitudinally from a proximal end to a spaced apart distal end and laterally from a first side to a second side, and wherein the separate layers cause the main body to have a different flexibility in the longitudinal direction than in the lateral direction.

3. The bone plate as recited in claim 1, further comprising a positioning marker disposed in or on the main body, the positioning marker being comprised of a radiopaque material.

4. The bone plate as recited in claim 3, wherein the positioning marker comprises an outline of the main body.

5. The bone plate as recited in claim 3, wherein the positioning marker comprises a metal powder mixed with one or more of the layers.

6. The bone plate as recited in claim 1, further comprising a screw locking mechanism disposed on the insert.

7. The bone plate as recited in claim 1, wherein the radiolucent material comprises a fiber and adhesive matrix.

8. The bone plate as recited in claim 7, wherein the fiber and adhesive matrix comprises a carbon fiber etherketone matrix.

9. The bone plate as recited in claim 1, wherein the plurality of separate layers comprises a first layer and a second layer, the fibers of the first layer being oriented in a different direction than the fibers of the second layer.

10. The bone plate as recited in claim 1, wherein the bone plate comprises a spinal plate.

11. A spinal stabilization system comprising:
a bone plate as recited in claim 1; and
a bone screw removably disposed within the passageway of the insert.

12. The bone plate as recited in claim 1, wherein the insert comprises a tubular stem disposed within the aligned first apertures, the flange outwardly projecting from the stem.

13. The bone plate as recited in claim 12, wherein the stem or flange of the insert forms a continuous circle.

14. The bone plate as recited in claim 1, wherein the plurality of separate layers are all compression molded together so that the separate layers are all bonded together.

15. The bone plate as recited in claim 1, further comprising a second middle layer disposed between the first layers and the second layers, the second middle layer having the first aperture extending therethrough, the first aperture of the second middle layer encircling an outer perimeter edge of the flange of the insert so that the second middle layer does not overlay the flange.

* * * * *